United States Patent [19]

Bukač et al.

[11] 3,962,239

[45] June 8, 1976

[54] METHOD FOR PRODUCING CYCLIC TRIMERS OF ORGANIC ISOCYANATES

[75] Inventors: Zbyněk Bukač; Jan Šebenda, both of Prague, Czechoslovakia

[73] Assignee: Ceskoslovenska akademie ved, Prague, Czechoslovakia

[22] Filed: Feb. 21, 1975

[21] Appl. No.: 551,514

[30] Foreign Application Priority Data
Feb. 28, 1974 Czechoslovakia................. 1478-74

[52] U.S. Cl. ....................................... 260/248 NS
[51] Int. Cl.² ....................................... C07D 251/34
[58] Field of Search............................. 260/248 NS

[56] References Cited
UNITED STATES PATENTS
3,578,662  5/1971  Cornell ............................. 260/248

Primary Examiner—John M. Ford
Attorney, Agent, or Firm—Burgess Ryan & Wayne

[57] ABSTRACT

The invention relates to a method for producing cyclic trimers of organic isocyanates from isocyanates employing as catalyst sodium dihydro-bis-/alkoxyethoxy/aluminates of the general formula

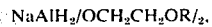

$NaAlH_2/OCH_2CH_2OR/_2$.

where R is $C_1$–$C_4$ alkyl group. The catalysts are soluble in the reaction solvent and consequently, the procedure is a desirable one because of its safety and easy handling and metering and the control of the strongly isothermic reaction is possible. Common cheap and relatively non-poisonous solvents which can be freed of water by distillation may be used as the reaction medium. The catalysts are used in the amount of 0.0005 to 0.05 moles per one mole of isocyanate.

13 Claims, No Drawings

METHOD FOR PRODUCING CYCLIC TRIMERS OF ORGANIC ISOCYANATES

The invention relates to a method for producing cyclic trimers of organic isocyanates by a catalyzed cyclotrimerization.

Cyclic trimers of organic isocyanates are useful in many applications, among them the technically important application in the field of macromolecular chemistry where these compounds are used for instance as a very effective cocatalysts for the anionic polymerization of lactams. See for example,/Czechoslovak Pat. application No. 5479-71/which corresponds to Czech Pat. No. 156,781 and British Pat. No. 1,360,899.

Cyclic trimers of organic isocyanates may be prepared in several ways. Practical production procedures consist in the utilization of numerous compounds as the catalysts of this cyclotrimerization reaction. See/H. Ulrich: Cycloaddition Reactions of Heterocumulenes, p. 122, Acad. Press, New York 1967/. The most effective catalysts are strongly basic compounds, for example alkali metal alkoxides. However, the application of these compounds is not suitable in plants because anhydrous alcohols and alkali metals or metal hydrides necessarily have to be used, which is inconvenient and also hazardous. Other similarly very effective compounds are complex hydrides of metals, e.g., sodium borohydride or lithium aluminum hydride according to U.S. Pat. No. 3,217,003, and the like. Handling of these compounds in production plants is also hazardous as in the case of alkali metal alkoxides. Another disadvantage resides in the fact that expensive solvents have to be used, such as for example dioxane, dimethoxyethane, etc., which must to be prepared in anhydrous and this makes the production process even more complex and costly. Further disadvantages of this procedure are low yields of cyclic trimers of isocyanates.

All the above mentioned shortcomings are overcome by the method for production of cyclic trimers of organic isocyanates according to the present invention, which consists in the addition of an organic isocyanate or its solution into a solution of a catalyst, i.e. sodium dihydro-bis/alkoxyethoxy/aluminate of the general formula

$$NaAlH_2/OCH_2CH_2OR/_2,$$

where R is alkyl with 1 to 4 carbon atoms. The catalyst is advantageously used in the amount of 0.0005 to 0.05 mole per one mole of isocyanate. The dimethoxy derivative is on the market under the registered trade mark Synhydrid as a highly concentrated benzene solution/-about 70 percent/.

The considerable advantage of application of the catalysts according to this invention is their safety and ease of comfortable metering. Another substantial advantage consists in the possible use of cheap and nonpoisonous aprotic solvents, for instance aliphatic hydrocarbons, as heptane, cyclohexane, extraction gasoline, and the like, or aromatic hydrocarbons, as benzene, toluene, xylene, and the like. These compounds are by themselves almost anhydrous and residual moisture may be removed by distillation which is a relatively cheap operation in comparison with drying of solvents e.g., according to U.S. Pat. No. 3,217,003. Another important advantage of the method according to this invention, is the possibility of the good control of the reaction which is strongly exothermic. This may be achieved by addition of an organic isocyanate which may be in the form of solution in a suitable solvent, into the heated solvent containing the catalyst at such a rate that the temperature of the reaction mixture is maintained below 110°-120° C. High yields, i.e., yields above 90 percent, are achieved by the procedure according to the invention. The method for producing cyclic trimers of organic isocyanates according to the invention is advantageous in comparison with the prior art methods not only because of the better control of the strongly exothermic reaction and high yields, but also in utilizing of cheaper solvents which can be more readily dried. The proposed procedure represents in this respect substantial technical progress as compared with the present state of knowledge.

The following examples illustrate the method according to the invention without, however, limiting its scope by any means.

EXAMPLE 1

A solution of 2.5 ml of Synhydrid/70% solution of sodium dihydro-bis-methoxyethoxy aluminate in benzene/in 750 ml of toluene was heated to 80°-90° C and 35 ml of phenylisocyanate was added at once under stirring, while the temperature spontaneously rose to 105°-110° C. Further, phenylisocyanate/215 ml/was added in such a rate, to maintain the temperature continuously at 105°-110° C. After all phenylisocyanate had been added, the reaction mixture was stirred at this temperature for an additional 30–60 min. After this period, no phenylisocyanate was present in the reaction mixture/absence of the absorbance at 2270 cm$^{-1}$/. The reaction mixture was allowed to cool and the separated product was filtered, washed with 100 ml of toluene and then washed three times with 100 ml portions of ethanol and dried. The yield was 96 percent of the theory. About 2 percent of further product was obtained by evaporation of mother liquors and crystallization from ethanol.

EXAMPLE 2

A toluene solution containing 70% of sodium dihydro-bis-methoxyethoxy aluminate/2 ml/was added to 500 ml of heptane. This solution was heated to 80° C and 25 ml of n-butylisocyanate was added at once under continuous stirring at this temperature. The residual 225 ml of n-butylisocyanate was then gradually added at such a rate that the reaction mixture was kept moderately boiling. After all of the isocyanate had been added, the mixture was stirred and heated to reflux for a further 30 min. The solvent was distilled off from the mixture and the residual product was distilled at 153°-154°C/2 Torr. The yield was 94% of pure tri-n-butyl isocyanurate.

EXAMPLE 3

Tricyclohexyl isocyanurate, tridodecyl isocyanurate and triethyl isocyanurate were prepared in the same way as in Example 2 in yields 91–97 percent of the theory.

EXAMPLE 4

Triphenyl isocyanurate was prepared in the yield of 93 percent of theory by the procedure given in Example 1, with the exception that sodium dihydro-bis-n-butoxyethoxy aluminate was used as the catalyst instead of sodium dihydro-bis-methoxyethoxy aluminate in the same amount.

We claim:

1. A method for producing cyclic trimers of organic isocyanates, wherein an organic isocyanate or its solution is added to a solution of the catalyst which is sodium dihydrobis-/alkoxyethoxy/aluminate of the formula $$NaAlH_2(OCH_2CH_2OR)_2,$$

where R is an alkyl group with 1 to 4 carbon atoms.

2. A method as set forth in claim 1, wherein the catalyst is used in an amount 0.0005–0.05 moles per one mole of isocyanate.

3. A method as set forth in claim 1, wherein aprotic solvents selected from the group consisting of aliphatic, cycloaliphatic and aromatic hydrocarbons are used as the solvents.

4. A method according to claim 1, wherein said organic isocyanate is phenyl isocyanate.

5. A method according to claim 1, wherein said organic isocyanate is n-butyl isocyanate.

6. A method according to claim 1, wherein said organic isocyanate is cyclo-hexyl isocyanate.

7. A method according to claim 1, wherein said organic isocyanate is dodecyl isocyanate.

8. A method according to claim 1, wherein said organic isocyanate is ethyl isocyanate.

9. A method according to claim 1, wherein said catalyst is sodium dihydro-bis-methoxyethoxy aluminate.

10. A method according to claim 1, wherein said addition of catalyst to said organic isocyanate solution is conducted at a temperature below 120°C.

11. A method according to claim 3, wherein said aromatic hydrocarbon is benzene.

12. A method according to claim 3, wherein said aliphatic hydrocarbon is heptane.

13. A method according to claim 1, wherein said catalyst is sodium dihydro-bis-n-butoxyethoxy aluminate.

* * * * *